United States Patent
Nagatsuka (10) Patent No.: US 12,140,552 B2
(45) Date of Patent: Nov. 12, 2024

(54) DYNAMIC IMAGING QUALITY CONTROL DEVICE, STORAGE MEDIUM, AND DYNAMIC IMAGING QUALITY CONTROL METHOD

(71) Applicant: Konica Minolta, Inc., Tokyo (JP)

(72) Inventor: Sumiya Nagatsuka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 501 days.

(21) Appl. No.: 17/360,118

(22) Filed: Jun. 28, 2021

(65) Prior Publication Data

US 2021/0404974 A1 Dec. 30, 2021

(30) Foreign Application Priority Data

Jun. 30, 2020 (JP) .................................. 2020-112257

(51) Int. Cl.
*G01N 23/04* (2018.01)
*A61B 6/00* (2006.01)
(Continued)

(52) U.S. Cl.
CPC .............. *G01N 23/04* (2013.01); *A61B 6/54* (2013.01); *G06T 7/0012* (2013.01); *A61B 6/583* (2013.01);
(Continued)

(58) Field of Classification Search
CPC ......... A61B 6/5217; A61B 6/463; A61B 6/50; A61B 6/486; A61B 5/08; A61B 6/503; A61B 6/507; A61B 6/4233; A61B 5/113; A61B 6/465; A61B 6/5235; A61B 6/563; A61B 6/5205; A61B 6/54; A61B 6/468; A61B 5/1135; A61B 6/487; A61B 6/5288;
(Continued)

(56) References Cited

U.S. PATENT DOCUMENTS

2014/0037072 A1* 2/2014 Han .................... G01N 23/087
378/207
2018/0089807 A1 3/2018 Reusch
(Continued)

FOREIGN PATENT DOCUMENTS

CN 102058432 A 5/2011
JP 2005205193 A 8/2005
(Continued)

OTHER PUBLICATIONS

JPO Notice of Reasons for Refusal for corresponding JP Application No. 2021-067579; Mail date: Apr. 26, 2022.
(Continued)

*Primary Examiner* — Ajibola A Akinyemi
(74) *Attorney, Agent, or Firm* — CANTOR COLBURN LLP (57) ABSTRACT

Provided is a dynamic imaging quality control device that performs quality control concerning dynamic imaging in which dynamics of a subject is imaged by sequential radiation emissions to the subject. The dynamic imaging quality control device includes a hardware processor. The hardware processor presents information on the quality control. The information on the quality control includes at least one of information on a framerate, information on a system sensitivity, and information on an image region.

19 Claims, 6 Drawing Sheets

(51) Int. Cl.
  *G06T 7/00* (2017.01)
  *A61B 6/58* (2024.01)

(52) U.S. Cl.
  CPC ............... *G01N 2223/3035* (2013.01); *G01N 2223/401* (2013.01); *G06T 2207/10116* (2013.01); *G06T 2207/30168* (2013.01)

(58) Field of Classification Search
  CPC ..... A61B 6/541; A61B 5/0095; A61B 5/0205; A61B 5/1128
  USPC .......................................................... 382/128
  See application file for complete search history.

(56) References Cited

U.S. PATENT DOCUMENTS

| | | | |
|---|---|---|---|
| 2018/0204326 A1* | 7/2018 | Noji | ..................... A61B 6/5217 |
| 2020/0287804 A1* | 9/2020 | Dalela | ................... H04L 43/067 |

FOREIGN PATENT DOCUMENTS

| | | |
|---|---|---|
| JP | 2008283531 A | 11/2008 |
| JP | 2009039410 A | 2/2009 |
| JP | 2010194116 A | 9/2010 |
| JP | 2012110399 A | 6/2012 |
| JP | 2013017594 A | 1/2013 |
| JP | 2015213681 A | 12/2015 |
| JP | 2019005013 A | 1/2019 |

OTHER PUBLICATIONS

Haraguchi et al., "CR Quality Management Program" Simple Check QC, Konica Minolta Technology Report, 2009, vol. 6 ; pp. 69-72; includes English abstract.
JPO Notice of Reasons for Refusal for corresponding JP Patent Application No. 2020-112257; Dated Dec. 8, 2020.
CNIPA Office Action for corresponding CN Application No. 202110724209.2; Issued on Jan. 26, 2022.
CNIPA The Second Office Action for corresponding CN Application No. 202110724209.2; Issued on Jul. 6, 2022.

* cited by examiner

```
DYNAMIC IMAGING
QUALITY CONTROL
        ↓
OBTAIN IMAGE DATA — S1
        ↓
CALCULATE VALUES — S21 ⎫
        ↓                ⎬
DETERMINE WHETHER VALUE IS — S22  } S2
APPROPRIATE                      ⎬
        ↓                ⎭
DETERMINE WHETHER VALUE — S23
RELATION IS APPROPRIATE
        ↓
PRESENT INFORMATION ON — S3
QUALITY CONTROL
        ↓
       END
```

FIG.4

|  |  | SECOND QUALITY INFORMATION ||||| 
|---|---|---|---|---|---|---|
|  |  | IMAGING | READOUT | TRANSFER | ANALYSIS | STORAGE |
| FIRST QUALITY INFORMATION | FRAMERATE |  |  |  |  |  |
|  | IMAGE QUALITY |  |  |  |  |  |
|  | IMAGE REGION |  |  |  |  |  |

VALUE, RELATION, APPROPRIATENESS, ETC.

DYNAMIC IMAGING QUALITY CONTROL DEVICE, STORAGE MEDIUM, AND DYNAMIC IMAGING QUALITY CONTROL METHOD

CROSS-REFERENCE TO RELATED APPLICATIONS

The present invention claims priority under 35 U.S.C. § 119 to Japanese Patent Application No. 2020-112257 filed on Jun. 30, 2020, the entire content of which is incorporated herein by reference.

BACKGROUND

Technological Field

The present invention relates to a dynamic imaging quality control device, a storage medium, and a dynamic imaging quality control method.

Description of the Related Art

Conventionally, there have been various techniques for quality control concerning static radiographic imaging.

For example, JP2008283531A discloses a radiographic image reading system including: a means to input image data to be a target of quality evaluation which is stored in a storage or read by an image reader; a means to input device identification information for identify the image reader or the storage used for the quality evaluation; a means to associate the input image data with quality evaluation identification information indicating the data for the quality evaluation and the device identification information; a means to store the image data associated with the quality evaluation identification information and the device identification information; a means to search and read the image data associated with the quality evaluation identification information and obtain evaluation results by arithmetic processing for the quality evaluation of the read image data; and a means to associate the obtained evaluation results with the device identification information associated with the image data and output the evaluation results.

In recent years, there have been developed various devices for dynamic imaging in which radiation is sequentially emitted to generate a dynamic image composed of multiple frames.

For example, JP2012110399A discloses a dynamic diagnosis support information generating system including: a radiation detector having detection elements arranged two-dimensionally and generating frame images sequentially by detecting the pulsed irradiation by the detection elements; and an analyzing means to calculate feature amounts of dynamics of a subject based on the frame images obtained by imaging the dynamics of the subject with the radiation source and the radiation detector.

SUMMARY

As in static imaging, a quality above some level is required in dynamic imaging in regard of prevention of problems such as misdiagnosis by doctors, overload on technicians by re-imaging, increase in the radiation dose by re-imaging, and the like.

However, as it hasn't been so long after dynamic imaging started to be used, sufficient research and development have not been attributed to quality control concerning dynamic imaging. For example, regular quality control after installation of devices is performed manually by technicians, dependent on individual skills, though more information on quality control is dedicated to dynamic imaging than static imaging. The efficiency improvement is therefore desired.

An object of the present invention is to enable efficient quality control concerning dynamic imaging with sequential irradiation.

To achieve at least one of the abovementioned objects, dynamic imaging quality control device reflecting one aspect of the present invention performs quality control concerning dynamic imaging in which dynamics of a subject is imaged by sequential radiation emissions to the subject, the dynamic imaging quality control device including:

a hardware processor;
wherein the hardware processor presents information on the quality control,
wherein the information on the quality control includes at least one of information on a framerate, information on a system sensitivity, and information on an image region.

To achieve at least one of the abovementioned objects, a non-transitory storage medium reflecting another aspect of the present invention stores a computer readable program for performing quality control of dynamic imaging in which radiation is sequentially emitted, wherein the program causes a computer to present information on the quality control,
wherein the information on the quality control includes at least one of information on a framerate, information on a system sensitivity, and information on an image region.

To achieve at least one of the abovementioned objects, dynamic imaging quality control method reflecting another aspect of the present invention for quality control of dynamic imaging in which radiation is sequentially emitted includes:

presenting information on the quality control,
wherein the information on the quality control includes at least one of information on a framerate, information on a system sensitivity, and information on an image region.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIGS. 5A-FIG. 5D show an example of a possible error in a dynamic image;

FIGS. 6A-FIG. 6C show another example of a possible error in a dynamic image;

FIGS. 7A-FIG. 7D show another example of a possible error in a dynamic image.

DETAILED DESCRIPTION OF THE EMBODIMENTS

Hereinafter, embodiments of the present invention are described with reference to the drawings. However, the scope of the present invention is not limited to the embodiments and illustrated examples.

<1. Radiographic Imaging System>

First described is an overall configuration of a radiographic imaging system (hereinafter referred to as a system 100) according to this embodiment.

Figure 1:
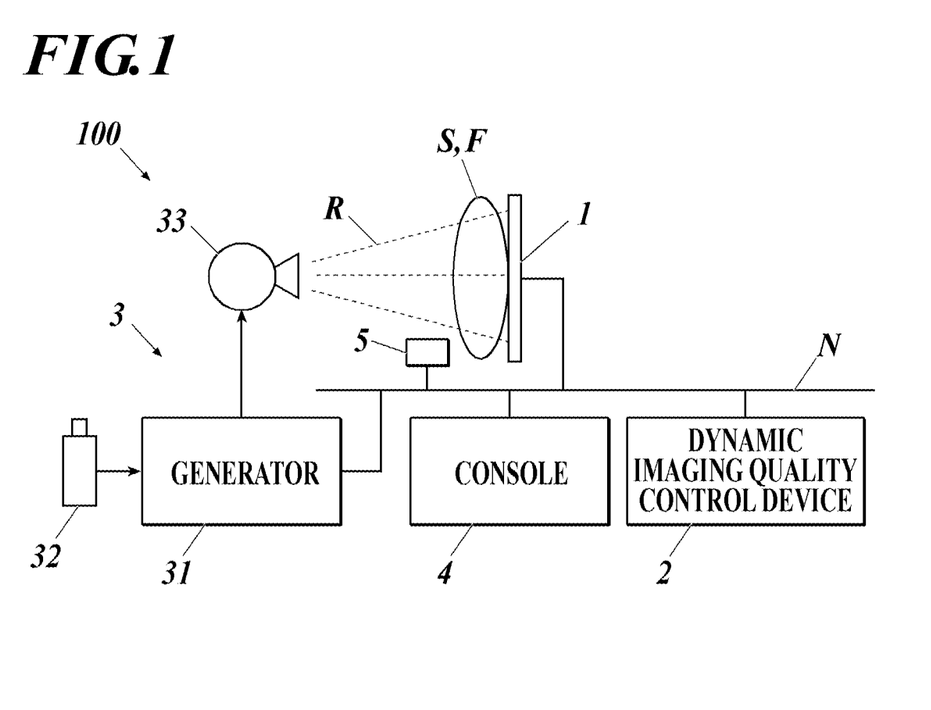
FIG. 1 is a block diagram showing a radiographic imaging system according to an embodiment of the present invention.

FIG. 1 is a block diagram of the system 100.

The system 100 includes a radiation detector 1 and a dynamic imaging quality control device (hereinafter referred to as a control device 2), as shown in FIG. 1.

The system 100 according to this embodiment further incudes a radiation generating device 3, a console 4, and an optical camera 5.

The devices 1 to 5 can communicate with each other via a communication network N (local area network (LAN), wide area network (WAN), the Internet, or the like, for example.

The system 100 may communicate with a hospital information system (HIS), a radiology information system (RIS), a picture archiving and communication system (PACS), a dynamics analysis device, and the like.

[1-1. Radiation Generating Device]

The radiation generating device 3 includes a generator 31, an irradiation command switch 32, and a radiation source 33.

The radiation generating device 3 may be installed in an imaging room, or may be movable together with the console 4 and the like by a mobile medical vehicle.

The generator 31 applies a voltage corresponding to a preset imaging condition(s) to the radiation source 33 (tube) in response to operation of the irradiation command switch 32. The preset imaging condition(s) includes, for example, a condition related to the subject S, such as a part to be imaged, imaging direction, and physique, or a condition related to radiation R irradiation such as tube voltage, tube current, irradiation time, and current time product (mAs value).

When a voltage is applied from the generator 31, the radiation source 33 generates radiation R (for example, X-rays) of a dose corresponding to the applied voltage.

The radiation source 33 can move in an X-axis direction, a Y-axis direction perpendicular to the X-axis, and a Z-axis direction perpendicular to the X-axis and the Y-axis. The radiation source 33 can further rotate around a rotation axis that is parallel to the Y-axis and a rotation axis that is parallel to the Z-axis to change the direction of the radiation irradiation port.

The radiation generating device 3 generates radiation R in a predetermined way according to a type of a radiographic image to be generated (a static image, a dynamic image composed of multiple frames).

For a static image, radiation R is emitted just one time in response to a single press of the radiation command switch 32.

For a dynamic image, radiation R is repeatedly emitted multiple times (pulsed) for a predetermined time (for example, 15 times for a second) in response to a single press of the radiation command switch 32. Alternatively, radiation R is continuously emitted for a predetermined time.

That is, the phrase "radiation is sequentially emitted" in the present invention indicates continuous irradiation in which radiation is continuously emitted, and pulsed irradiation in which radiation is intermittently emitted.

[1-2. Radiation Detector]

Though not shown in the drawings, the radiation detector 1 includes the followings: a sensor substrate in which pixels having radiation detection elements and switch elements are arranged in a two-dimensionally (in a matrix shape); a scanning circuit that switches on/off of the respective switch elements; a readout circuit that reads out the amount of charge released from the respective pixels as signal values; a control unit that generates a radiographic image based on the signal values read by the readout circuit; a communication unit that transmits the generated radiation image data and various signals to the outside and receives various kinds of information and various signals; and the like. In response to receiving radiation, the radiation detection element generates electric charge according to the dose, and the switch elements store and release electric charge.

The radiation detector 1 generates a radiographic image according to the dose of the emitted radiation R by accumulating and releasing electric charges and reading the signal values in synchronization with the timing of the radiation R from the radiation generating device 3.

In generating a static image, a radiographic image is generated just one time in response to a single press of the radiation command switch 32.

In generating a dynamic image, a frame of a radiographic image is repeatedly generated multiple times for a predetermined time (for example, 15 times for a second) in response to a single press of the radiation command switch 32.

The radiation detector 1 may store and transfer a generated dynamic image in the form of image data, or may display it in real-time on the display connected to the radiation detector 1.

For example, in fluoroscopy, images are displayed in real-time.

[1-3. Console]

The console 4 sets various imaging conditions (a tube voltage, tube current, irradiation time (milliampere-second value), imaged region, imaging direction, etc.) in at least one of the radiation detector 1 and the radiation generating device 3.

The console 4 includes a personal computer (PC) and a dedicated device.

The console 4 sets the imaging conditions according to imaging order information obtained from other system(s) (HIS, RIS, etc) or operation by users (for example, technicians).

[1-4. Dynamic Imaging Quality Control Device]

The control device 2 performs quality control concerning dynamic imaging.

"Dynamic imaging" indicates a series of operations (execution of program(s)) of the system 100 including: emission of radiation R by the radiation generating device 3; generation and transfer of a dynamic image by the radiation detector 1; transfer of the dynamic image between the devices; analysis by the dynamics analysis device; and storage of the dynamic image in a data storage (a cloud server, PACS, etc.). The analysis by the dynamics analysis device may be analysis of, for example, ventilation, blood flow, and structures (motions of structures such as bones and internal organs).

The "quality control" indicates not only quality control by regular quality checking after device installation but also quality assurance at the time of device installation.

The control device 2 includes a personal computer (PC) includes a dedicated device.

Though the control device 2 and the console 4 are separately provided in the system 100 shown in FIG. 1, the control device 2 may be integrated with the console 4.

In a case where a dynamic analysis device or a PACS not shown in the drawings are provided in the system 100, the control device 2 may be integrated with those devices.

The control device 2 is described later in detail.

[1-5. Optical Camera]

The optical camera 5 optically images a phantom F in parallel with radiographic imaging for obtaining a dynamic image of the phantom F for quality checking.

In the case where the phantom F is not used in quality checking (a dynamic image obtained by imaging of a subject is used in quality checking), the optical camera 5 may be omitted.

[1-6. Outline of Operations of Radiographic Imaging System]

The system 100 configured as described above operates as follows.

First, radiation R is emitted by the radiation generating device 3 to a diagnosis target region of a subject S positioned in the interval between the radiation source 33 of the radiation generating device 3 and the radiation detector 1 facing each other. The radiation detector 1 then generates a (static, dynamic) radiographic image(s) and sends image data of the radiographic image to at least one of the control device 2 and the console 4.

Upon receipt of the image data, the control device 2 executes the dynamic imaging quality control process (described later in detail) and sends the image data to another data storage.

<2. Details of Dynamic Imaging Quality Control Device)

Next, the control device 2 in the above-described system 100 is described in detail.

Figure 2:
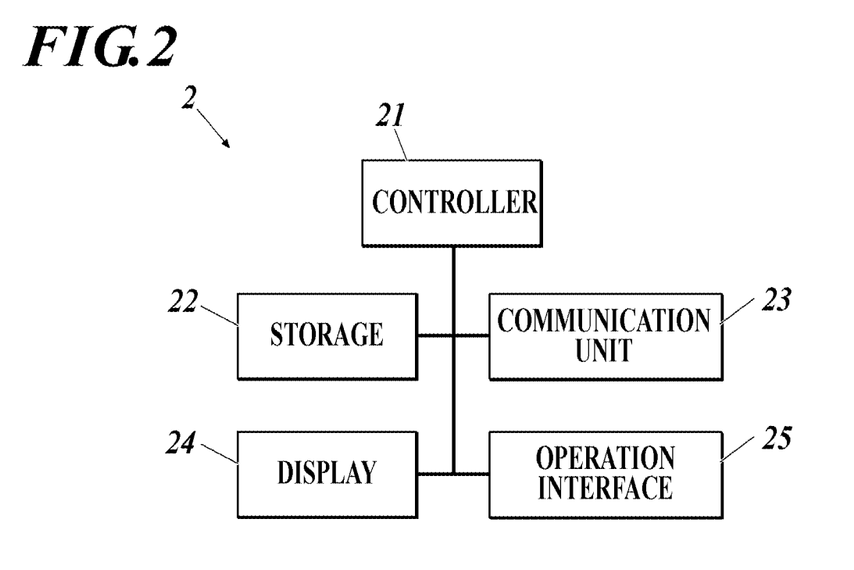
FIG. 2 is a block diagram showing a dynamic imaging quality control device in the radiographic imaging system in FIG. 1.
Figure 3:
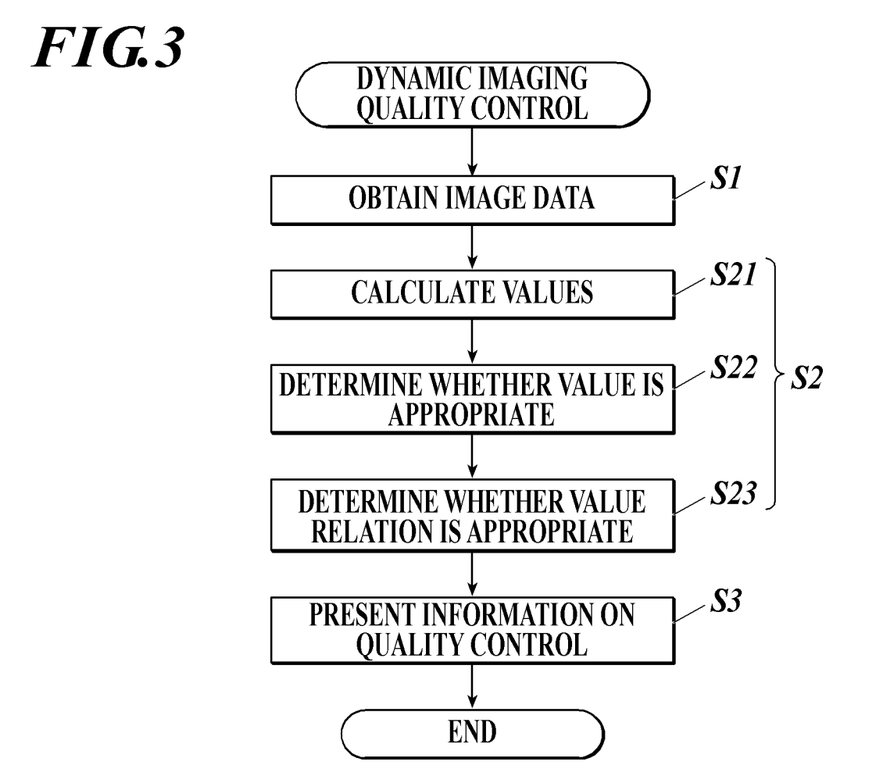
FIG. 3 is a flowchart of a dynamic imaging management process executed by the dynamic imaging quality control device in FIG. 2.
Figure 4:
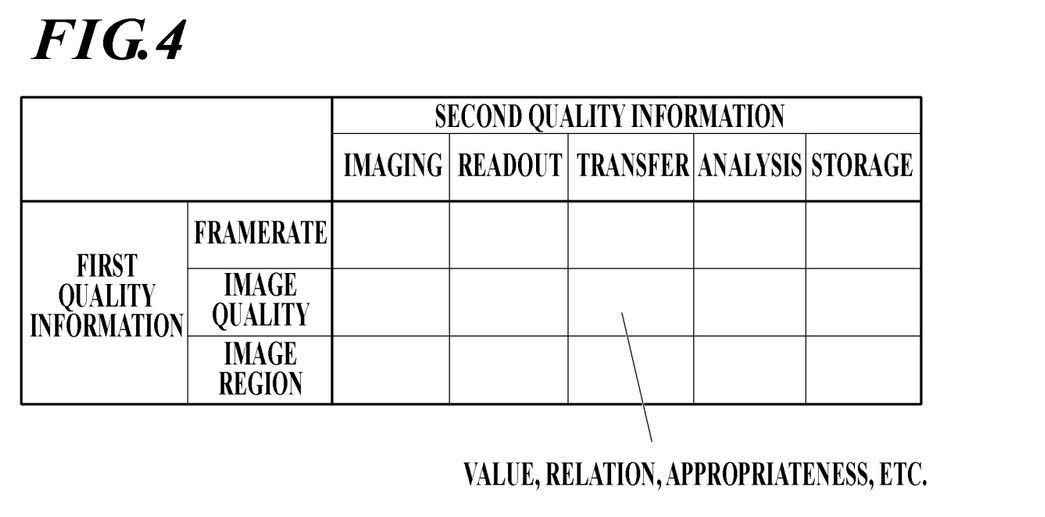
FIG. 4 is a table showing information on quality control presented by the dynamic imaging quality control device in FIG. 2.

FIG. 2 is a block diagram showing the control device 2. FIG. 3 is a flowchart of the dynamic imaging quality control process executed by the control device 2. FIG. 4 is a table showing information on quality control presented by the control device 2. FIG. 5 to FIGS. 7A-FIG. 7D show exemplary errors which may appear in dynamic images. FIG. 8 shows an exemplary screen displayed by the control device 2.

[2-1. Configuration of Dynamic Imaging Quality Control Device]

The control device 2 includes, as shown in FIG. 2, a controller 21 (hardware processor), a storage 22, a communication unit 23, a display 24, and an operation interface 25.

The components 21 to 25 are electrically connected with each other by a bus or the like.

The controller 21 includes a central processing unit (CPU), and a random access memory (RAM).

The CPU of the controller 21 reads various programs stored in the storage 22, loads them in the RAM, executes various processes according to the loaded programs, and centrally controls the operation of each of the units of the control device 2.

The storage 22 includes a non-volatile memory and a hard disk.

The storage 22 stores various programs (including the dynamic imaging quality control program) executed by the controller 21, parameters necessary for executing the programs, and the like.

The storage 22 may store image data of radiographic images obtained from other device(s).

The communication unit 23 includes a communication module.

The communication unit 23 sends and receives various signals and data to and from the other devices (the radiation detector 1, the console 4, etc.) connected by wire or wirelessly via a communication network N (a local area network (LAN), a wide area network (WAN), the Internet, etc.).

The display 24 displays various screens used in diagnosis by users.

The display 24 includes, for example, a liquid crystal display (LCD), an electronic luminescent display (ELD), and a cathode ray tube (CRT).

The display 24 displays radiographic images according to image signals received from the controller 21.

The operation interface 25 is an operating means operable by users.

The operation interface 25 includes a keyboard (cursor keys, number input keys, various function keys, etc.), a pointing device (a mouse, etc.), and a touch panel superimposed on the surface of the display 24.

The operation interface 25 outputs control signals according to operation by users to the controller 21.

The control device 2 may not necessarily include the display 24 or the operation interface 25, and may receive control signals from an input device provided separately from the control device 2 or output image signals to a display device (a monitor) provided separately from the control device 2, via the communication unit 23, for example.

In the case where a device(s) other than the control device 2 (the console 4 or the like) includes a display or an operation interface, the control device 2 may receive control signals via an operation interface of the other device or output image signals to a display of the other device (a display and operation interface may be shared with other devices).

[2-2. Operations of Dynamic Image Quality Control Device]

When predetermined conditions are satisfied, the controller 21 of the control device 2 configured as described above executes the dynamic imaging quality control process as shown in FIG. 3, for example.

The predetermined conditions include, for example, turning on the power of the control device 2, obtaining image data from other device(s), receiving a predetermined control signal from other device(s), and receiving a predetermined input via the operation interface 25.

In the dynamic imaging quality control process, the controller 21 executes an obtaining step (Step S1).

At the obtaining step, the controller 21 obtains image data to be the target of quality checking.

The methods of obtaining the image data include receiving via the communication unit 23, reading out from the storage 22, and reading out from a medium.

In the case where the dynamic imaging quality control process is executed when the image data is obtained, the obtaining step is omitted.

The image data obtained at the obtaining step may be of an image obtained by imaging of an actual subject (medical image) or an image obtained by imaging a phantom F (image for quality checking).

The phantom F may be dedicated to evaluation of the radiographic imaging system or some object other than that.

Especially, the phantom F for dynamic imaging may be any object that moves periodically (for example, a clock, metronome, etc.).

After having obtained the image data, the controller 21 executes an analyzing process for quality control concerning dynamic imaging (Step S2).

In the analyzing process, the controller 21 analyzes the obtained image data and extracts information on the quality control concerning dynamic imaging.

The information on the quality control includes the first quality information on a dynamic image obtained by dynamic imaging or the second quality information on functions or operations of at least one of the devices used in dynamic imaging.

The information concerning the quality control may include information on the phantom F.

The first quality information includes information on at least one of a framerate, a system sensitivity, and an image region.

The system sensitivity includes a detection sensitivity of the radiation detector 1 and an output dose of the radiation generator.

The first quality information according to this embodiment includes all the above information.

The first quality information described above includes information specific to dynamic images (not applicable to static images), but may include information common to static images (at least one of, for example, a size, sharpness, linearity, dynamic range, low contrast resolution, system sensitivity, uniformity, and erasability).

The second quality information includes information on at least one of: generation of a dynamic image; transfer of a dynamic image; analysis of a dynamic image; and storage of a dynamic image.

The second quality information according to this embodiment includes all the above information.

The information on generation of a dynamic image includes information on imaging in which the radiation generating device 3 emits radiation R to emulate charge in the radiation detector 1 and readout of a radiographic image by the radiation detector 1.

The information on transfer of a dynamic image may be divided into information on transfer from the radiation detector 1 to the console 4, that from the radiation detector 1 to the control device 2, and that from the console 4 to the control device 2.

The information on storage of a dynamic image may be divided into information on storage in the radiation detector 1, that in the console 4, that in the control device 2, that in another data storage, and the like.

The information on the quality control according to this embodiment is indicated in each section formed by intersection of rows and columns, where the column contains the first quality information and the row contains the second quality information, in a table (matrix) as shown in FIG. 4, for example.

Specifically, the information on the quality control includes an analysis result(s) at the time of at least one of generation (imaging, readout), transfer, analysis, and storage of an image.

The analysis result includes a value of at least one of a framerate, a system sensitivity, and an image region, information on whether the value is appropriate, and information on a relation with a value at the time of at least any other of the operations.

In the analyzing process, the controller 21 calculates a value of at least one of a framerate, a system sensitivity, or an image region (Step S21).

For example, in the case where the second quality information includes information on a framerate, the controller 21 calculates a time interval (gap in generation time) between a frame and the next or previous frame for multiple frames (preferably all frames) of a dynamic image.

In the case where the second quality information includes information on a system sensitivity, the controller 21 calculates an index value indicating the sensitivity (for example, at least one of detective quantum efficiency (hereinafter referred to as DQE), an SN ratio, an amount of lag components in signal values) on multiple frames (preferable all frames) of a dynamic image.

The controller 21 may detect presence or absence of an artifact A instead of or in addition to calculation of the above index value.

In the case where the second quality information includes information on an image region, the controller 21 calculates a position of a subject region where the subject S is imaged (coordinates of specified pixels of the subject region) on multiple frames (preferably all frames) of a dynamic image.

In the analyzing process according to this embodiment, the controller 21 determines whether the above-described calculated value is appropriate (Step S22).

For example, in the case where the frame intervals are calculated, the controller 21 compares each of the calculated values of the intervals with a setting value (a reciprocal of the framerate). If the calculated value matches the setting value, the controller 21 determines that the frame interval is appropriate, and if the calculated value does not match the setting value, the controller 21 determines that the frame interval is not appropriate.

The calculated interval value does not necessarily completely match the setting value, and the controller 21 may determine that the calculated value is appropriate within a range of $\pm\alpha$ % of the setting value.

The value $\alpha$ may be appropriately modified by users.

In the case where dynamic imaging of the phantom F is performed, the controller 21 compares the action of the phantom F in a dynamic image with the action of the phantom F on an optical image(s) obtained beforehand by optical imaging of the phantom F performing the accurate actions, and determines that the imaging is appropriate if the actions match each other and that it is not appropriate if the actions do not match each other.

The action of the phantom F on the dynamic image does not necessarily completely match the action of the phantom F on the optical image(s), and the controller 21 may determine that the imaging is appropriate if a gap between the actions is within a range of $\pm\alpha$ % of a width in the direction of the action of the phantom F.

The value $\alpha$ may be appropriately modified by users.

In the case where the frame intervals in the dynamic image described above are not appropriate even though the action of the phantom F on the dynamic image matches the action of the phantom F on the optical image, the phantom F is defective.

In the case where the index values indicating the sensitivity are calculated, the controller 21 compares the calculated index value of each frame with the index value of the next or previous frame, and determines that the sensitivity is appropriate if the index values match each other and that the sensitivity is not appropriate if the index values do not match each other.

The calculated index value of a frame does not necessarily completely match the index value of the previous or next frame, and the controller 21 may determine that the sensitivity is appropriate within a range of $\pm\alpha$ % of the setting value.

The value $\alpha$ may be appropriately modified by users.

In the case where the artifact A is detected in a frame, the controller 21 determines whether the detected artifact A is different from the artifact in the previous or next frame.

In the case where the positions of the subject region are calculated, the controller 21 compares the position of the subject region in each frame with the position of the subject region in the next or previous frame, and determines that the position is appropriate if a gap in the position is within a range of the reference value and that the position is not appropriate if a gap in the position is out of the range of the reference value.

The reference value may be smaller or greater within a range of ±α %.

The value α may be appropriately modified by users.

In the analyzing process according to this embodiment, the controller 21 determines whether the relation of values at the time of at least two of generation (imaging, readout), transfer, analysis, and storage of an image is appropriate (consistency) (Step S23).

For example, in the case where the frame intervals are calculated, the controller 21 compares framerates (reciprocals of the calculated values) at the time of at least two of generation (imaging, readout), transfer, analysis, and storage of a dynamic image, and determines that the frame interval is appropriate if the framerates match each other and that the frame interval is not appropriate if the framerates do not match each other.

The controller 21 may compare a calculated value and a value set on the system 100 (included in the header information of the dynamic image) and determine whether the values match each other.

In the case where the controller 21 determines that predetermined information on the quality control is not appropriate in the analyzing process according to this embodiment, the controller 21 extracts check items concerning the predetermined information.

Figure 5A:
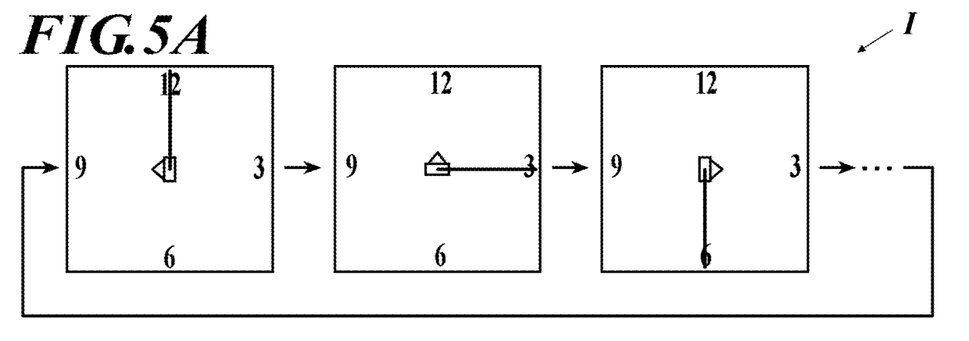
Figure 5B:
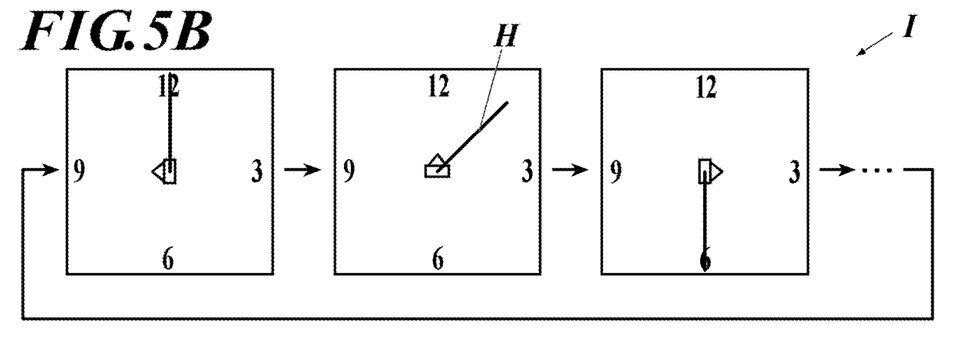
Figure 5C:
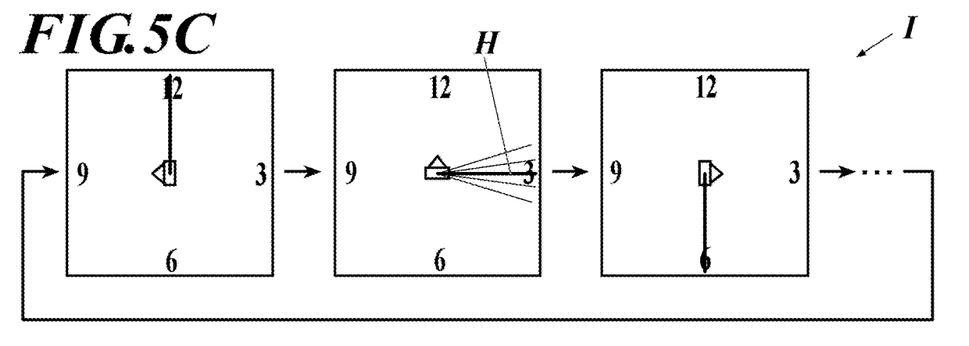
Figure 5D:
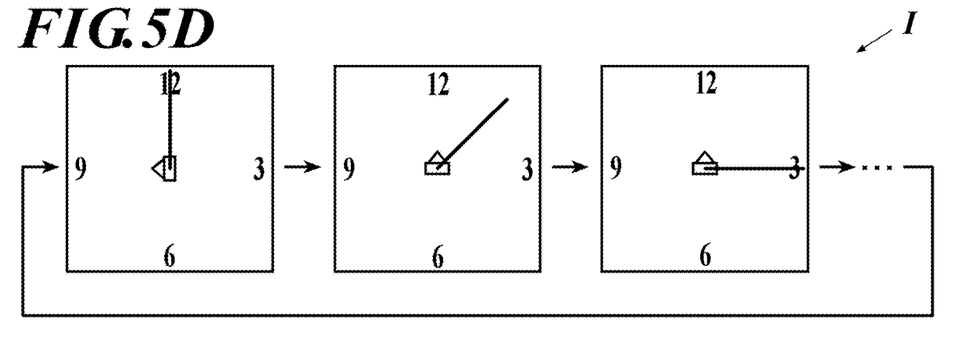

For example, in the case where, as a result of analysis of a dynamic image I, at least one of the calculated values of frame intervals do not match the setting value, the dynamic image I obtained at the obtaining step may often include, compared to an image on which the action of the subject S (clock) is correctly imaged as shown in FIG. 5A, a frame taken at an incorrect timing (for example, the position of the hand H is mispositioned from the intended position) as shown in FIG. 5B, a frame having a motion blur (for example, the hand H is plurally shown together) as shown in FIG. 5C, or all frames taken at an incorrect timing as shown in FIG. 5D.

The dynamic image shown in FIG. 5B may result from, for example, a readout error on the radiation detector 1, or an operation error of the phantom F.

The dynamic image shown in FIG. 5C may result from, for example, an irradiation timing error on the radiation generating device 3 (for example, several emissions instead of one pulse), or an operation error of the phantom F.

The dynamic image shown in FIG. 5D may result from, for example, an erroneous setting in the device 1 or 3, an operation error of the phantom F.

In the case where it is determined as a result of analysis that the dynamic image I includes a frame taken at an incorrect timing as shown in FIG. 5B, the controller 21 extracts at least one of following check items: whether the readout operation of the radiation detector 1 is normal; and whether the operation of the phantom F is normal.

In the case where it is determined that the dynamic image I includes a frame having a motion blur as shown in FIG. 5C, the controller 21 extracts at least one of following check items: whether the radiation emission of the radiation generating device 3 is normal; and whether the operation of the phantom F is normal.

In the case where all frames of the dynamic image I are taken at incorrect timings as shown in FIG. 5D, the controller 21 extracts at least one of following check items: whether the setting of the device 1 and/or 3 is appropriate; and whether the operation of the phantom F is normal.

Figure 6A:
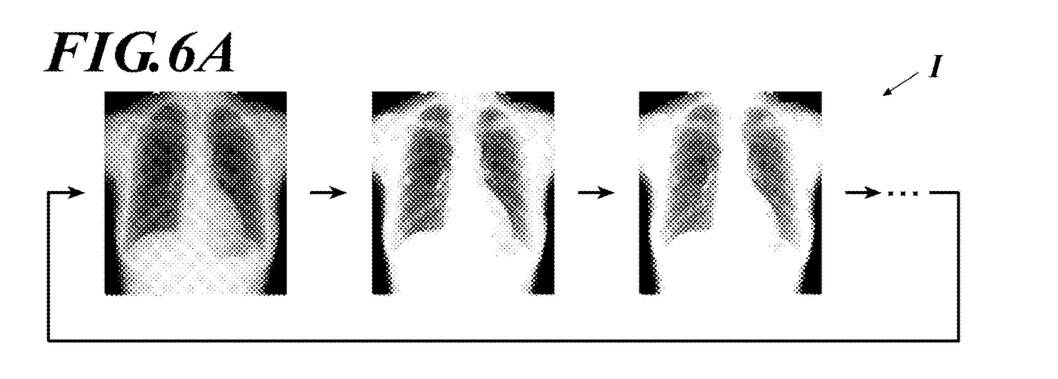
Figure 6B:
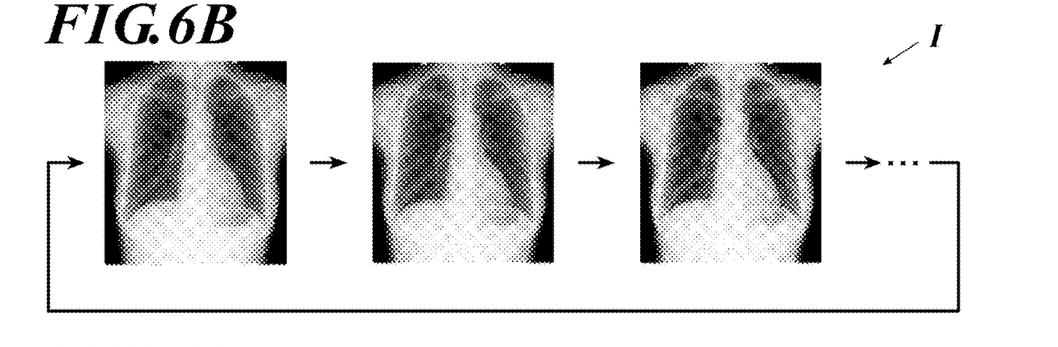
Figure 6C:
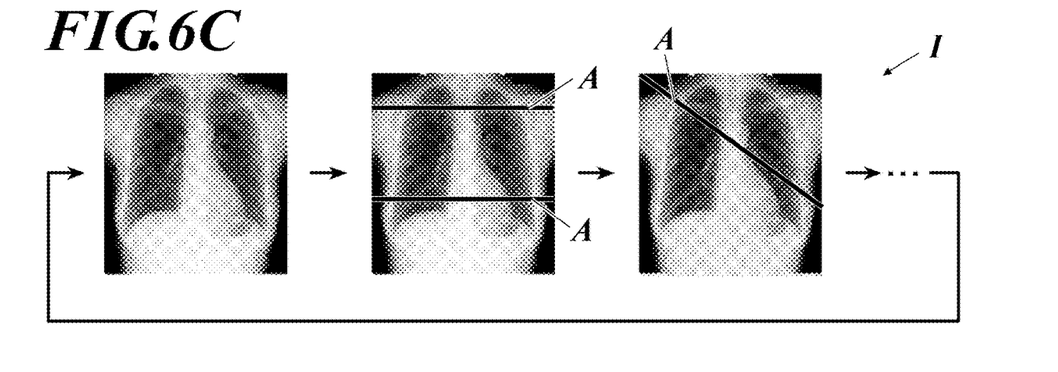

In the case where, as a result of analysis of a dynamic image I, the index value indicating the sensitivity of a frame does not match the index value of the previous or next frame, the dynamic image I obtained at the obtaining step may often include signal values varying by frames (gradually lighter/darker) as shown in FIG. 6A, for example, include SN values varying by frames (gradually blurred) as shown in FIG. 6B, or a frame on which an artifact A is taken as shown in FIG. 6C.

The dynamic images I as shown in FIG. 6A and FIG. 6B may result from, for example, a readout error on the radiation detector 1, an irradiation error on the radiation generating device 3, or an image correction error.

The dynamic image I as shown in FIG. 6C may result from, for example, a readout error on the radiation detector 1 or an appearance of an artifact A due to an image correction error.

In the case where it is determined as a result of analysis of a dynamic image I that the signal values vary by frames as shown in FIG. 6A, the controller 21 extracts at least one of following check items: whether the irradiation operation (dose) of the radiation generating device 3 is normal; whether the readout operation of the radiation detector 1 is normal; whether the setting of the radiation generating device 3 is appropriate (mAs value, etc.); and whether the image correction processing of the image correction device (the radiation detector 1, the console 4, the analyzing device, etc.) is normal.

In the case where it is determined that the dynamic image I includes SN values varying by frames as shown in FIG. 6B, the controller 21 extracts at least one of following check items: whether the irradiation operation (dose) of the radiation generating device 3 is normal; whether the setting (tube voltage, etc.) of the radiation generating device 3 is appropriate; whether the readout operation of the radiation detector 1 is normal; and whether the image correction operation of the image correction device is normal.

In the case where it is determined that the dynamic image I includes a frame on which an artifact A is taken as shown in FIG. 6C, the controller 21 extracts at least one of following check items: whether the readout operation of the radiation detector 1 is normal; and whether the image correction processing of the image correction device is normal.

Figure 7A:
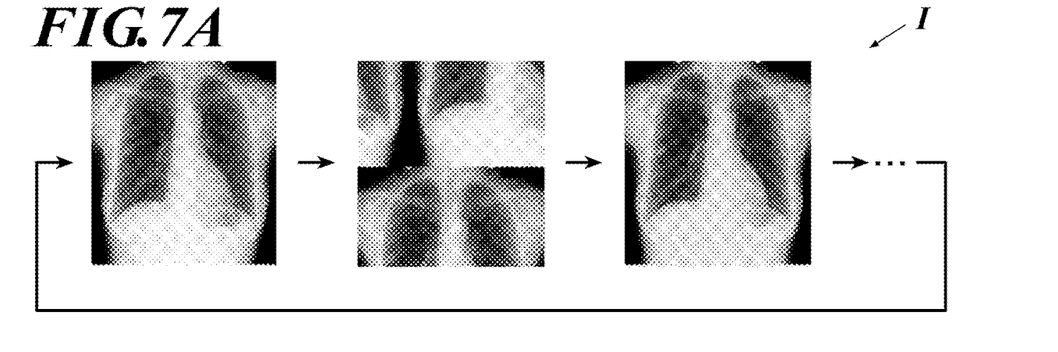
Figure 7B:
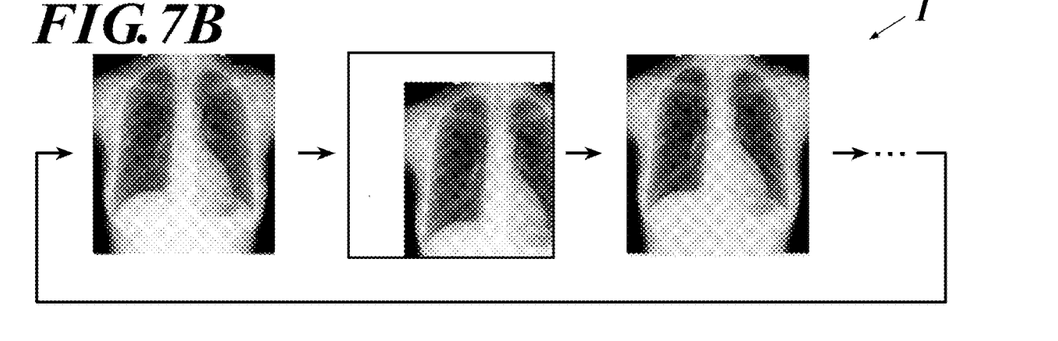
Figure 7C:
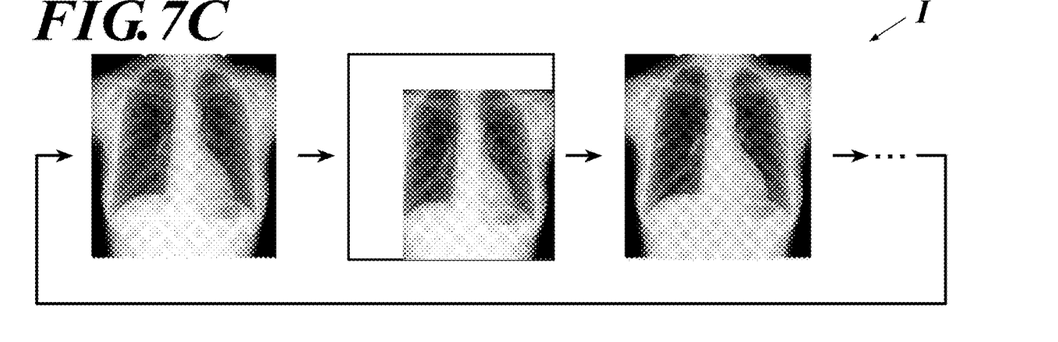
Figure 7D:
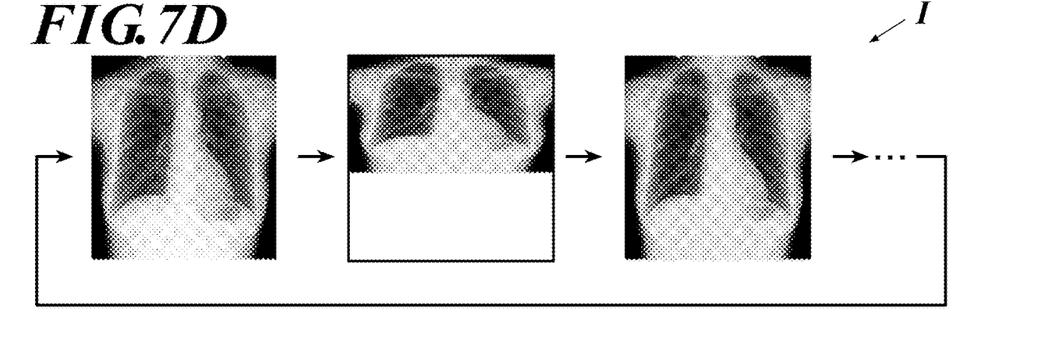
Figure 8:
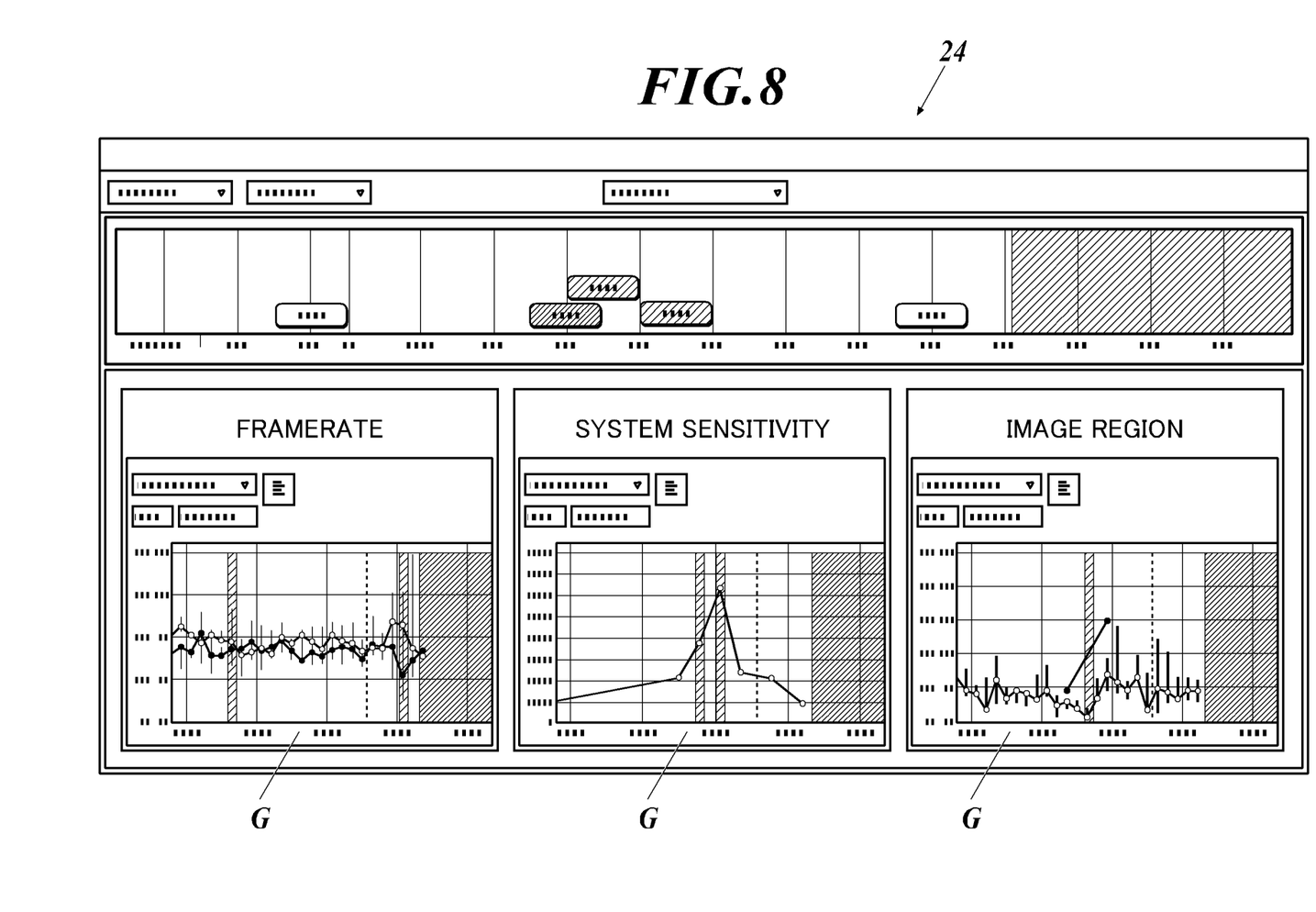
FIG. 8 shows an example of a screen displayed by the dynamic imaging quality control device in FIG. 2.

In the case where, as a result of analysis of a dynamic image I, the calculated position of the subject region does not match those in the previous and next frames, the dynamic image I obtained at the obtaining step may include, for example, a frame on which the upper side and the lower side of the image are switched as shown in FIG. 7A, a frame on which part of the image is cut out due to displacement of the whole image as shown in FIG. 7B, a frame on which part of the image is cut out without displacement as shown in FIG. 7C, or a frame with a different aspect ratio as shown in FIG. 7D.

The dynamic image I as shown in FIG. 7A may result from, for example, a transfer error between devices, a storage error on the data storage device, and the like.

The dynamic images I as shown in FIGS. 7B and 7D may result from, for example, a readout error on the radiation detector 1, or a storage error on the data storage device.

The dynamic image I as shown in FIG. 7C may result from, for example, displacement of the position of emission of radiation R.

In the case where, as a result of analysis of a dynamic image I, it is determined that the dynamic image I includes a frame on which the upper side and the lower side of the image are switched as shown in FIG. 7A, the controller 21 extracts at least one of following check items: whether the transfer operation on the devices 1 to 4 is normal; and whether the storage operation on the data storage device is normal.

In the case where it is determined that the dynamic image I includes a frame on which part of the image is cut out due to displacement of the whole image or a frame with a different aspect ratio s shown in FIG. 7B and FIG. 7D, the controller 21 extracts at least one of following check items: whether the readout operation on the radiation detector 1 is normal; and whether the storage operation on the data storage device is normal.

In the case where it is determined that the dynamic image I includes a frame on which part of the image is cut out without displacement of the image as shown in FIG. 7C, the controller 21 extracts a check item: the position of emission of radiation R from the radiation generating device 3.

The check items may be extracted by referring to a table stored in the storage 22 in advance showing relations between analysis results and check items (possible causes) or by inputting the present analysis results in a machine learning model that is trained on analysis results as input objects and check items as output objects.

The controller 21 executes the analyzing process described above as an analyzing means.

After having analyzed the quality of dynamic imaging, the controller 21 executes the quality control presenting process (Step S3).

In the quality control presenting process, the controller 21 presents information on the quality control to users.

In the quality control presenting process according to this embodiment, the controller 21 displays the information on the quality control on the display 24 to present the information.

The controller 21 may send the information on the quality control to other device(s) (for example, the console 4, etc.) and display the information on the display of the other device.

In the quality control presenting process according to this embodiment, the controller 21 presents the analysis results in the above-described analyzing process (values, relations of values, determination on whether the values or relations are appropriate, etc.).

Specifically, the information is presented in a form of the table shown in FIG. 4.

In the quality control presenting process, the controller 21 may present analysis results in the previous analysis to users.

In that case, the controller 21 may show the analysis results in the present analysis and the past analyses including the previous one in a graph G as shown in FIG. 8, for example.

This makes it possible to easily see whether the state of the system 100 has changed or not since the last quality checking until the present quality checking.

In the case where the analysis results indicate that some information among the information on the quality control is not adequate in the above-described analyzing process, the controller 21 presents to users the check items about the information not adequate.

In the quality controller 21 presenting process, the controller 21 may present to users a reason(s) why the analysis results indicate that some information is not adequate.

Specifically, the controller 21 displays: a frame that has different values than the other frames (a frame interval, DQE, position of the subject region, etc.); a frame number of that frame; a text indicating how that frame is different from the other frames (for example, "frame interval reduction between Nth and (N+1)th frames"); a dynamic image I that has values different from images at the other steps; a text indicating the step where the values change (for example, "frame rate reduction at the timing of transfer"); and the like.

When the analysis results indicate that the information on the quality control is adequate in the analyzing process, the controller 21 presents to users that dynamic imaging is ready, in the quality control presenting process according to this embodiment.

In the quality control presenting process according to this embodiment, when all the information on the quality control is adequate, the controller 21 presents to users that dynamic imaging is ready.

This makes it possible to prevent users from carrying out dynamic imaging when the system 100 has a problem.

If a predetermined part of the information is adequate even though some part of the information on the quality control is not adequate, the controller 21 may present to users that dynamic imaging is ready.

The controller 21 executes the quality control presenting process described above as a quality control presenting means.

As the controller 21 according to this embodiment presents the information on the quality control by displaying the information on the display 24, the display 24 also functions as a part of the quality control presenting means according to this embodiment.

<3. Effects>

As described hereinbefore, the control device 2 or the system 100 including the control device according to this embodiment presents the information on the quality control to users.

Thus, the control device 2 or the system 100 makes it possible to effectively perform the quality control concerning dynamic imaging.

<4. Misc.>

Needless to say, the present invention is not limited to the above embodiment and can be appropriately modified without departing from the scope of the present invention.

For example, the control device 2 or the system 100 according to the above-described embodiment performs the quality control concerning dynamic imaging only, but the control device 2 and the system 100 may perform both the quality control concerning dynamic imaging and quality control concerning static imaging.

The control device 2 according to the above-described embodiment performs the analyzing process and the quality control presenting process. However, if the system 100 includes the dynamic analysis device, the dynamic analysis device may perform the analyzing process and the control device may perform the quality control presenting process based on the analysis result.

The above description discloses an example of using a hard disk, a semiconductor nonvolatile memory and the like as the computer readable medium of the program according to the present invention. However the present invention is not limited to the example. A portable recording medium such as a CD-ROM can be used as other computer readable mediums. A carrier wave is also applied as a medium providing the program data according to the present invention via a communication line.

What is claimed is:

1. A dynamic imaging quality control device that performs quality control concerning dynamic imaging in which dynamics of a subject is imaged by sequential radiation emissions to the subject, the dynamic imaging quality control device comprising:
   a hardware processor;
   wherein the hardware processor presents information on the quality control,
   wherein the information on the quality control includes at least one of information on a framerate, information on a system sensitivity, and information on an image region, and
   wherein the information on the quality control is presented during quality assurance at a time of an installation of a device for dynamic imaging, or during quality checking after the device is installed.

2. The dynamic imaging quality control device according to claim 1,
   wherein the information on the quality control includes at least one of information on generation of a dynamic image obtained by the dynamic imaging, information on transfer of the dynamic image, information on analysis of the dynamic image, and information on storage of the dynamic image.

3. The dynamic imaging quality control device according to claim 1,
   wherein the information on the quality control includes at least two of information on generation of a dynamic image obtained by the dynamic imaging, information on transfer of the dynamic image, information on analysis of the dynamic image, and information on storage of the dynamic image.

4. The dynamic imaging quality control device according to claim 3,
   wherein the information on the quality control includes information on correspondence of framerates at two or more timings of the generation of the dynamic image, the transfer of the dynamic image, the analysis of the dynamic image, and the storage of the dynamic image.

5. The dynamic imaging quality control device according to claim 1,
   wherein the hardware processor performs analysis of quality of the dynamic imaging,
   wherein the information on the quality control includes an analysis result obtained by the analysis.

6. The dynamic imaging quality control device according to claim 5,
   wherein the analysis result includes an adequacy analysis result about whether each content of the information on the quality control is adequate.

7. The dynamic imaging quality control device according to claim 6,
   wherein the hardware processor presents that the dynamic imaging is ready in response to the adequacy analysis result indicating that a predetermined content of the information on the quality control is adequate.

8. The dynamic imaging quality control device according to claim 6,
   wherein the hardware processor presents a check item regarding a content of the information on the quality control which is inadequate according to the analysis result.

9. The dynamic imaging quality control device according to claim 8,
   wherein the hardware processor presents a reason why the content is inadequate according to the analysis result.

10. The dynamic imaging quality control device according to claim 5,
    wherein the hardware processor presents the analysis result of previous analysis.

11. The dynamic imaging quality control device according to claim 1,
    wherein the information on the quality control includes information on a phantom.

12. The dynamic imaging quality control device according to claim 1,
    wherein the device for the dynamic imaging is a radiation detector or a radiation generating device.

13. A non-transitory storage medium storing a computer readable program for performing quality control of dynamic imaging in which radiation is sequentially emitted,
    wherein the program causes a computer to present information on the quality control,
    wherein the information on the quality control includes at least one of information on a framerate, information on a system sensitivity, and information on an image region, and
    wherein the information on the quality control is presented during quality assurance at a time of an installation of a device for dynamic imaging, or during quality checking after the device is installed.

14. The non-transitory storage medium storing the computer readable program according to claim 13,
    wherein the information on the quality control includes at least one of information on generation of a dynamic image obtained by the dynamic imaging, information on transfer of the dynamic image, information on analysis of the dynamic image, and information on storage of the dynamic image.

15. The non-transitory storage medium storing the computer readable program according to claim 13,
    wherein the program causes the computer to perform analysis of quality of the dynamic imaging.

16. The non-transitory storage medium storing the computer readable program according to claim 15,
    wherein the analysis includes adequacy analysis about whether each content of the information on the quality control is adequate.

17. The non-transitory storage medium according to claim 13,
    wherein the device for the dynamic imaging is a radiation detector or a radiation generating device.

18. A dynamic imaging quality control method for quality control of dynamic imaging in which radiation is sequentially emitted, the method comprising:
    presenting information on the quality control,
    wherein the information on the quality control includes at least one of information on a framerate, information on a system sensitivity, and information on an image region, and
    wherein the information on the quality control is presented during quality assurance at a time of an installation of a device for dynamic imaging, or during quality checking after the device is installed.

19. The dynamic imaging quality control method according to claim 18,
wherein the device for the dynamic imaging is a radiation detector or a radiation generating device.

* * * * *